United States Patent [19]

Sawa et al.

[11] 4,325,912

[45] Apr. 20, 1982

[54] CARBON MONOXIDE DETECTION APPARATUS

[75] Inventors: Kenneth B. Sawa, Yorba Linda; Radhakrishna M. Neti, Brea, both of Calif.

[73] Assignee: Beckman Instruments, Inc., Fullerton, Calif.

[21] Appl. No.: 165,164

[22] Filed: Jul. 1, 1980

[51] Int. Cl.³ .................... G01N 27/16; G01N 27/18
[52] U.S. Cl. ........................................ 422/95; 422/94; 422/98; 23/232 E
[58] Field of Search ................ 23/232 E; 422/94, 95, 422/96, 97, 98; 338/34; 73/23, 27

[56] References Cited

U.S. PATENT DOCUMENTS

| | | | |
|---|---|---|---|
| 3,200,011 | 8/1965 | Baker | 422/94 |
| 3,564,474 | 2/1971 | Firth et al. | 422/95 |
| 4,072,467 | 2/1978 | Jones | 422/97 |
| 4,118,193 | 10/1978 | Neti et al. | 422/94 |
| 4,123,225 | 10/1978 | Jones | 422/98 |
| 4,128,458 | 12/1978 | Obiaya | 422/94 |

*Primary Examiner*—Ronald Serwin
*Attorney, Agent, or Firm*—R. J. Steinmeyer; Paul R. Harder; Edward C. Jason

[57] ABSTRACT

A carbon monoxide detection apparatus and process are disclosed in which the amount of carbon monoxide is measured by oxidizing it and measuring the heat of oxidation. To accomplish this platinum oxide is used as the catalyst and an operating temperature is maintained at which oxidation of carbon monoxide occurs in the presence of platinum oxide. Various types of heat-change-responsive techniques are disclosed, including measurement of the voltage drop across forward-biased solid-state diodes, and measurement of the voltage generated by thermo-couples.

19 Claims, 4 Drawing Figures

CARBON MONOXIDE DETECTION APPARATUS

BACKGROUND OF THE INVENTION

This invention relates to carbon monoxide (CO) detectors, and particularly to those which use an oxidation process and heat change measurement for sensing the amounts of carbon monoxide.

One of the important concerns relates to automotive exhaust measurements, wherein the gas flow is continuous. Sensitivity, quick response, and accuracy become particularly important where the CO content of the gas under investigation may be changing frequently and by significant amounts.

Various types of CO detectors have been proposed and some have been commercialized, but none have provided all of the desired characteristics. Some of the techniques used have been spectrophotometric, spectrochemical, and electrochemical. Another class of detectors, known as solid-state detectors, uses metal oxides which chemisorb CO, resulting in a change of the electronic properties of the metal oxides, which change is measured by detected current or resistance changes.

Another approach, which the present invention utilizes, is oxidation of the CO, accompanied by measurement of the temperature changes caused by oxidation. This has been attempted before, as evidenced by such patents as Lanneau U.S. Pat. No. 3,560,160; Brown et al. U.S. Pat. No. 4,036,592; Jones U.S. Pat. No. 4,072,467; and Jones et al. U.S. Pat. No. 4,123,225.

It appears that the prior art temperature-responsive detectors are deficient in various respects, primarily due to the problem of "poisoning" of the catalysts used to promote the oxidation process. The term "poisoning" refers to the loss of effectiveness of the catalyst material caused by its reaction with CO and/or other gases to which it is exposed. As such poisoning occurs, the reliability of the detector is diminished or destroyed because of reduction in the ability of the catalyst to cause the oxidation of CO. All of the catalysts proposed by the patents cited above are subject to the "poisoning" problem, including hopcalite, manganese oxide, cupric oxide, platinum-rhodium alloys, platinum, and palladium.

In general, the purpose of the present invention is to provide a carbon monoxide detector which will not have the shortcomings of prior art detectors, and will possess the following characteristics: (1) linear response over a wide range of CO concentration, (2) adaptability for either portable or stationary analyzers, (3) cost competitiveness, and (4) relative freedom from most of the common interferences.

SUMMARY OF THE INVENTION

The present invention is derived primarily from the discovery that a significantly improved temperature-responsive carbon monoxide detector can be provided by using platinum oxide as the catalyst.

Related aspects of the invention concern the way in which the platinum oxide is incorporated into the detector in order to accomplish the best results.

Another aspect of the invention relates to the use of the oxides of other noble metals as catalysts in CO detectors.

DETAILED DESCRIPTION OF THE DRAWINGS

DETAILED DESCRIPTION OF THE DISCLOSED EMBODIMENTS

The prior art catalysts used in carbon monoxide detectors generally fell into one of two categories—either noble metals, such as palladium, platinum or rhodium, used in the non-oxidized state; or oxides of base metals, such as manganese oxide, cupric oxide or silver oxide.

There was apparently no awareness, or reason to suspect, that an oxide of a noble metal, such as platinum oxide, would have a highly advantageous effect when used as the catalyst in a CO detector responsive to the heat of oxidation.

Platinum oxide has been used as a catalyst in other oxidation environments. For example, U.S. Pat. No. 4,118,193, disclosing an invention of the present inventors, refers to the use of platinum oxide (PtO) as a catalyst in a catalytic reactor system and method used for removing interferents such as reactive hydrocarbons.

The developmental work leading to the present invention grew partially out of observations made by the inventors during work on the invention disclosed in U.S. Pat. No. 4,118,193. They observed that the catalytic reactor of the patent did not discharge any measurable amount of CO. Although the reason for that phenomenon was not apparent at that time, subsequent experimental work leading to the present invention demonstrated that platinum oxide, used as a catalyst under suitable conditions, causes substantially complete oxidation of the carbon monoxide in sample gas mixtures, such as those from an automobile exhaust. By maintaining the correct temperature, a process is performed in which the CO gas alone is oxidized in the detector, thereby permitting the amount of temperature change to be translated into a determination of the percentage of CO in the gas mixture being analyzed.

According to the understanding of the present inventors, the reaction involving the PtO catalyst and the CO in the detector are two fold. At the preferred temperature of operation, 180° C., oxygen does not react with carbon monoxide. However, platinum oxide, as a catalyst, reacts with the carbon monoxide and gives up its oxygen according to the following equation:

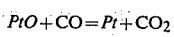

$$PtO + CO = Pt + CO_2$$

The sample stream must also contain at least stoichiometric amounts of oxygen, which simultaneously reacts with the ionic platinum to regenerate the platinum oxide according to the following equation:

$$O_2 + 2Pt = 2PtO$$

In the course of these reactions heat is given up which produces a temperature change in the platinum oxide.

Because of the regeneration of the PtO, its catalytic function in the detector does not diminish with use, so the detector continues to provide reliable information, and there is no need for recharging the catalyst.

Figure 1:
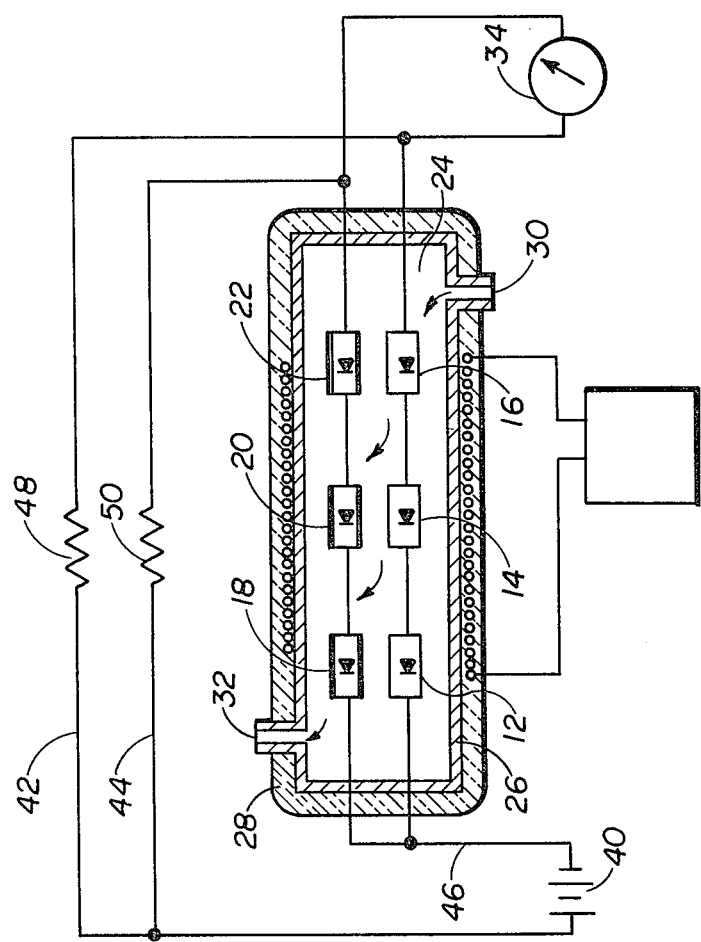
FIG. 1 is a schematic showing of a CO detector incorporating the present invention, in which the temperature-measuring structure is shown in cross section.
Figure 3:
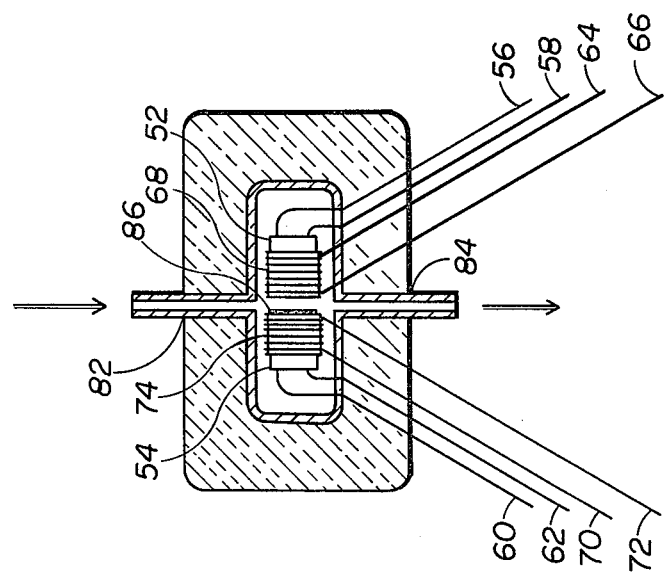
FIG. 3 shows a modified version of the invention, in which a different means is used to maintain the substantially constant elevated temperature of the detector.

Various arrangements may be used to convert the temperature change caused by CO oxidation into information concerning the amount of CO in the sample. Three of those arrangements are illustrated in the drawings. FIGS. 1 and 3 show versions of the invention in which the heat change due to CO oxidation causes a change in the voltage drop across one or more series-connected solid-state diodes in forward bias. An increasing temperature at each diode reduces its forward-biased voltage drop, and a decreasing temperature at each diode increases its forward-biased voltage drop. For satisfactory operation, diodes must be used which do not drop too low in forward-biased voltage under the operating temperatures of the detector. A satisfactory diode for this purpose is the 1N458A supplied by Texas Instruments.

As shown in FIG. 1, three reference diodes 12, 14 and 16 are connected in series in one circuit, and three measuring diodes 18, 20 and 22 are connected in series in a parallel circuit. All six of the diodes are located in a temperature-maintaining chamber 24, which is carefully constructed and controlled to maintain the desired operating temperature, at which temperature the oxidation of CO will occur when PtO is the catalyst. The enclosure which forms chamber 24 may, as shown, comprise an inner liner 26 and a heating blanket 28. The liner 26 should be made of a nonmetallic, nonreactive material, such as Teflon, ceramic, or glass, which will not react with the gases in the chamber. The heating blanket 28 may be of any suitable type. For example, a satisfactory blanket is manufactured by Brisk Heat Co., which comprises quartz wool containing heating elements, a high temperature fabric on the outside covering the quartz wool, and quartz or silica cloth on the inside next to liner 26.

Chamber 24 has an inlet port 30 to receive the entering gas, the CO content of which is to be determined, and an outlet port 32 through which the gas is exhausted after oxidation and measurement of the CO contained therein.

The number of diodes used is an arbitrary selection. It may vary from one reference diode and one measuring diode to many reference diodes and many measuring diodes, the number of reference and measuring diodes being the same so their voltage drops can be usefully compared. The advantage of using several diodes in series is the addition of their voltage drops to increase the sensitivity of the detector, which is responsive to the total voltage drop, as measured by a millivolt meter 34.

It is theoretically possible to dispense with the reference diodes, and use only measuring diodes. However, the results are more accurate when reference diodes are used, because they respond to temperature changes not caused by CO oxidation. Thus unavoidable variations in the temperature inside chamber 24, due, for example, to changes in temperature of the entering gas, are compensated for in the comparison of the voltage drop across the measuring diodes with the voltage drop across the reference diodes.

The reference diodes 12, 14 and 16 are responsive to the temperature existing in chamber 24, independently of the CO content of the gas in the chamber. The gas is in contact with the enclosures, or housings, of the reference diodes, and the temperature is reflected in the voltage drop across the p-n junction of each reference diode.

The measuring diodes 18, 20 and 22, which may also be described as sensing elements, are coated with platinum oxide to cause the CO-related reactions (oxidation) at the surfaces of the measuring diodes.

Figure 2:
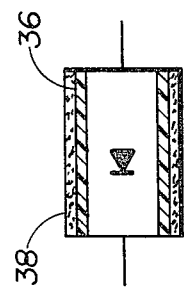
FIG. 2 is a closeup of one of the diodes of FIG. 1, showing the layers of epoxy and catalyst applied thereto.

FIG. 2 is a closeup of a measuring diode, showing a greatly magnified view of the diode coating. In order to cause adhesion of the PtO catalyst material to the enclosure, or housing, of the diode, a thin layer 36 of thermally conducting epoxy, preferably silver epoxy, is applied to the outer surface of the measuring diode. It is desirable that the silver epoxy layer 36 be as thin as possible. However, the layer 36 should be continuous and uniform, and should be capable of permanently holding the PtO coating on the measuring diode. It appears that the thickness range of the silver epoxy layer 36 may be varied from 0.001 inch to 0.1 inch without altering the effectiveness of the detector, but, as stated above, it is preferred that a very thin layer be used. The silver epoxy layer 36 has essentially two functions—serving as an adhesive for the PtO coating, and providing an effective heat transfer agent. As stated above, oxidation of the silver in the epoxy would be detrimental. Therefore, excessive quantities of silver should be avoided because the silver might be oxidized to silver oxide and enter into reaction with the CO, thereby giving rise to two different kinds of reaction rates, one between the PtO and CO, and the other between the AgO and the CO.

The platinum oxide is applied as a layer 38 on top of the epoxy layer 36. It is desirable to maximize the amount of the PtO because of its catalyst function, but the thickness of the PtO layer 38 is limited by the requirement that the PtO be in direct adhesive contact with the epoxy in order to prevent flaking off of the PtO. In practice, the PtO has been applied as a powder having a mesh of approximately 300; and it has been sprinkled onto the epoxy surface while the latter is still in a "tacky" condition. The thickness of the PtO coating 38 which will adhere to the epoxy layer 36 can be increased up to about 0.010 inch. The catalyst layer 38 preferably is continuous and uniform in thickness.

After the platinum oxide layer 38 has been applied to the silver epoxy layer 36, the epoxy must be cured to prevent flaking of the catalyst. Curing may be accomplished by heating the device to 60°–70° C., and maintaining that temperature for 4–6 hours. Other curing temperatures and periods may be developed, if desired.

Referring again to FIG. 1, it is apparent that the layers of PtO on the measuring diodes 18, 20 and 22 will cause a temperature differential between those diodes and the reference diodes 12, 14 and 16, if there is CO in the sample gas mixture, and if the temperature of the detector is maintained at such a level that the PtO catalyst causes oxidation of the CO. This temperature differential is manifested in a reduced forward-biased voltage drop across the measuring diodes, as compared to the forward-biased voltage drop across the reference diodes. The forward-biased voltage drop across the p-n junction of each measuring diode will vary by approximately 2 millivolts per degree Centigrade.

As shown, both the measuring diodes and the reference diodes are in forward bias in the electrical circuit.

The positive terminal of a power source 40 is connected by a conductor 42 to the anodes of the series-connected reference diodes, and by a conductor 44 to the anodes of the series-connected measuring diodes. The cathodes of all the diodes are connected by conductor 46 to the negative terminal of the power source 40.

A balanced bridge circuit may be used to cause the millivolt meter 34 to measure the voltage differences between the series-connected reference electrodes and the series-connected measuring electrodes. Conductor 42, which is in the reference diode branch of the circuit, and which has a resistor 48 connected therein, is connected to one terminal of meter 34. Conductor 44, which is in the measuring diode branch of the circuit, and which has a resistor 50 connected therein, is connected to the other terminal of meter 34. The values of resistors 48 and 50 are equal.

In operation, the temperature of chamber 24 is maintained at a desired value, preferably 180° C. The CO in the sample gas in the chamber, which would normally not oxidize at that temperature, is caused to oxidize by the presence of the platinum oxide catalyst. This causes a temperature increase of the measuring diodes, which in turn causes a proportional variation in the voltage drop across the measuring diodes, which is measured by the meter 34. As the percentage of CO in the sample gas varies, the heat of oxidation will vary, and the temperature of the measuring diodes will vary. Assuming suitable calibration of the detector, the signals at meter 34 may be translated into information as to the percentage of the CO in the sample gas. Response of this CO detector has proved to be linear over a CO concentration range from approximately 3 ppm to 10,000 ppm.

The temperature variation due to oxidation of the carbon monoxide is very small in relation to the stable operating temperature maintained in the chamber. The change due to oxidation is approximately 0.01° C. for 50 ppm of CO. Because of this small change which is being measured, it is considered very desirable and/or necessary to use reference diodes for comparison purposes, to carefully maintain the basic operating temperature, and to use a multiplicity of series-connected diodes.

Although 180° C. has been identified as the desired stable operating temperature of chamber 24, there is a range of suitable temperatures, depending primarily on the rate of flow of sample gas through the chamber. If the rate of flow is relatively high, a higher chamber temperature must be maintained in order to insure complete CO oxidation; whereas a lower rate of flow permits a lower chamber temperature to be used. At a flow rate of 400 cc/minute, the preferred chamber temperature is 180° C., as previously indicated. Depending on the flow rate, the stable temperature maintained in chamber 24 may be selected in a range from a minimum of about 160° C. to a maximum of about 300° C.

Because amounts of hydrogen will usually be present in the gas sample, and because hydrogen will oxidize at a lower temperature than carbon monoxide, the hydrogen should be removed from the gas sample before it enters the carbon monoxide detector. This can be accomplished by causing oxidation of the hydrogen in a separate upstream chamber having a suitable operating temperature, and suitable catalyst materials, for causing oxidation of the hydrogen without causing oxidation of the carbon monoxide.

FIG. 3 discloses a second embodiment of the invention, which is considered the preferred embodiment because its electrical power requirements for heating are so much lower than those of the first embodiment. In FIG. 3, an array of series-connected reference diodes is mounted in a metal casing, or enclosure, 52; and a parallel array of series-connected measuring diodes is mounted in a metal casing, or enclosure, 54. The anode side of the reference diodes is connected by a conductor 56 to the positive terminal of the power source; and their cathode side is connected by a conductor 58 to the negative terminal of the power source. The anode side of the measuring diodes is connected by a conductor 60 to the positive terminal of the power source; and their cathode side is connected by a conductor 62 to the negative terminal of the power source. The detector circuitry may utilize the same bridge circuit and millivolt meter as the first embodiment. The number (say 6–8), and type, of diodes is the same in the reference and measuring arrays.

Heating of the separate reference and measuring diode arrays is accomplished by heater coils wound around the outside of the respective diode array housings. Conductors 64 and 66 lead to opposite ends of a reference array heating coil 68; and conductors 70 and 72 lead to opposite ends of a measuring array heating coil 74. The two coils 68 and 74 are identical, and their temperature is stabilized at the desired level by means of a regulated d.c. power supply.

The two diode arrays may be located in a temperature-maintenance chamber 76 formed in a ceramic housing 78 supported in an Eccofoam heat-insulating outer portion 80. An inlet port 82 receives the incoming gas and an outlet port 84 permits the exhaust gas to leave the chamber.

A layer 86 of the platinum oxide catalyst is secured to the inner face of the enclosure 54 which contains the measuring diode array. This layer of PtO is secured to the enclosure 54 by a suitable heat-conducting layer of adhesive, such as silver epoxy. No layer of catalyst is secured to the inner face of enclosure 52 which contains the reference diode array. Therefore, oxidation of CO in the sample gas will increase the temperature of the measuring diode array but not of the reference diode array. The distance between the measuring diode array and the reference diode array must be sufficient, preferably at least 1/16 inch, to prevent heat transfer between them. (The same minimum separation must exist between the measuring and reference diodes in FIG. 1)

As stated above, the embodiment of FIG. 3 has the advantage of relatively low power requirements in maintaining the desired operating temperature in chamber 76. It has functioned at a power consumption of 600 mW, and could drop the power requirements as low as 400 mW, provided the sample gas flow rate is sufficiently low (approximately 50 cc/minute). The embodiment of FIG. 1 requires a much higher power consumption. For example, the experiments conducted with that version of the invention utilized 85 watts; however, design refinements could reduce that figure somewhat.

The temperature-responsive measuring means used in the previous embodiments are not the only available means for responding to the heat of oxidation in the CO detector. While the foregoing embodiments of the invention have utilized the voltage drop across solid state diodes as the temperature-change-measuring means, such other means may be used as thermo-couples, thermistors, or heater-sensor assemblies wherein the decrease in power required to maintain a constant temperature is measured.

Figure 4:
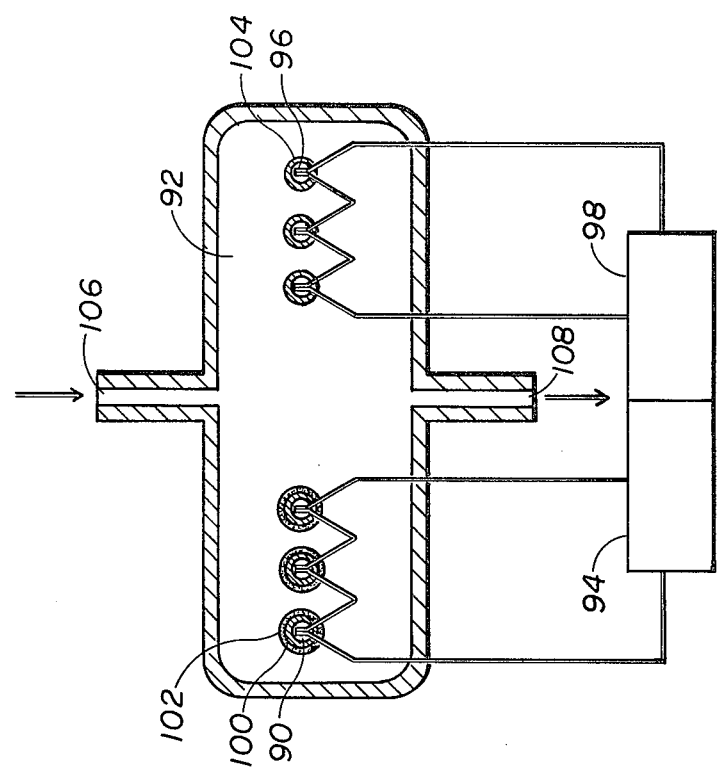
FIG. 4 is a cross-sectional view of another modified version of the invention, wherein thermocouples are used as temperature-responsive devices instead of the diodes used for that purpose in the versions shown in the previous figures.

FIG. 4 discloses an embodiment of the invention in which the temperature change is measured by a copper-constantin thermo-couple. One or more series-connected measuring thermo-couple junctions 90 are located inside a temperature-maintenance chamber 92, and are electrically connected to one channel 94 of a recorder. An equal number of series-connected reference thermo-couple junctions 96, also located inside chamber 92, are electrically connected to the other channel 98 of the same recorder. The measuring thermo-couples 90 are each buried in a bead 100 of silver epoxy, which is coated with a layer 102 of platinum oxide catalyst. The reference thermo-couples 96 are not coated with a layer of catalyst, but preferably are each buried in a bead 104 of silver epoxy, in order that the measuring and reference thermo-couple junctions will be identical, except for the presence of the catalyst at the measuring junctions and the absence of the catalyst at the reference junctions.

Comparing the electrical measurements of recorder channels 94 and 98 provides an indication of the amount of CO in the sample gas, which enters through port 106 and exhausts through port 108. The temperature of chamber 92 is maintained at the approximate stable operating temperature needed to provide the catalytic reaction of the CO and PtO. The sensitivity of each thermo-couple junction is very much lower than the sensitivity of each solid-state diode in the embodiments of FIGS. 1 and 3. The average response of the thermo-couple junction is approximately 0.04 mV per degree Centigrade, whereas the average response of the diode p-n junction is approximately 2 mV per degree Centigrade.

The oxides of nobel metals other than platinum should have similar results if used as catalysts in the measurement of CO by measuring the heat due to oxidation of the CO. This includes palladium oxide, gold oxide, and the oxides of rhodium, iridium and rhenium. Each of those oxides would have its own temperature at which the catalytic reactions with carbon monoxide would occur. So the appropriate operating temperature would have to be maintained in the chamber where the CO oxidation occurs.

The following claims are intended not only to cover the specific embodiments disclosed, but also to cover the inventive concepts explained herein with the maximum breadth and comprehensiveness permitted by the prior art.

What is claimed is:

1. A carbon monoxide detector comprising;
   (a) at least one forward biased solid-state measuring diode connected to provide a first output signal;
   (b) an equal number of forward biased solid-state reference diodes connected to provide a second output signal;
   (c) a deposit of an oxide of a noble metal in heat conducting relationship to the measuring diode, said deposit serving as an catalyst for carbon monoxide oxidation; and
   (d) electrical means for generating an output signal that varies in accordance with the difference between the first and second output signals.

2. A carbon monoxide detector as set forth in claim 1 in which the noble metal is platinum.

3. A carbon monoxide detector as set forth in claim 1 in which said deposit is a coating applied to the body of each measuring diode.

4. A carbon monoxide detector as set forth in claim 1 in which the measuring diodes are mounted in a metal casing and in which said deposit is applied to the casing.

5. A carbon monoxide detector as set forth in claim 1 in which the operating temperature of the diodes is in the range of 160° C. to 300° C.

6. A carbon monoxide detector as set forth in claim 2 in which the operating temperature of the diodes is approximately 180° C.

7. A carbon monoxide detector as set forth in claim 1, 2, 5 or 6 in which the detector is supplied with a sample gas that contains enough oxygen to prevent any carbon monoxide therein from reducing the noble metal oxide to the noble metal.

8. A carbon monoxide detector as set forth in claim 1 in which the deposit is held in place by a layer of a thermally conducting epoxy.

9. A carbon monoxide detector comprising:
   (a) a plurality of series-connected measuring thermo-couple junctions coated with an oxide of a noble metal;
   (b) an equal number of series-connected reference thermocouple junctions not coated with an oxide of a noble metal;
   (c) electrical means for comparing the total voltage at the measuring thermocouple junctions with the total voltage at the reference thermocouple junctions.

10. A carbon monoxide detector as set forth in claim 9 in which the noble metal is platinum.

11. A carbon monoxide detector as set forth in claim 9 in which the operating temperature of the thermocouple junctions is in the range of 160° C. to 300° C.

12. A carbon monoxide detector as set forth in claim 10 in which the operating temperature of the thermocouple junctions is approximately 180° C.

13. A carbon monoxide detector as set forth in claim 9, 11 or 12 in which the detector is supplied with a sample gas that contains enough oxygen to prevent any carbon monoxide therein from reducing the noble metal oxide to the noble metal.

14. A carbon monoxide detector as set forth in claim 9 in which the oxide is held in place by a layer of a thermally conducting epoxy.

15. A carbon monoxide detector comprising:
   (a) at least one temperature responsive measuring element connected to provide a first signal;
   (b) an equal number of temperature responsive reference elements connected to provide a second signal;
   (c) casing means for mounting the measuring elements and the reference elements;
   (d) a temperature maintenance chamber surrounding the casing means, the chamber having an inlet and an outlet;
   (e) means for regulating the temperature inside the temperature maintenance chamber;
   (f) a deposit of a noble metal oxide on said casing means in heat conducting relationship to the measuring elements and not in heat conducting relationship to the reference elements;
   (g) said inlet and outlet being arranged to direct a flow of a sample gas across the deposit; and
   (h) means for generating an output signal that varies in accordance with the difference between said first and second signals.

16. A carbon monoxide detector as set forth in claim 15 in which the temperature inside the temperature maintenance chamber is between 160° C. and 300° C.

17. A carbon monoxide detector as set forth in claim 15 in which the noble metal is platinum and in which the temperature inside the temperature maintenance chamber is approximately 180° C.

18. A carbon monoxide detector as set forth in claim 15, 16 or 17 in which the detector is provided with a sample gas that contains enough oxygen to prevent the reduction of the noble metal oxide to the noble metal.

19. A carbon monoxide detector as set forth in claim 15 in which the noble metal is platinum.

* * * * *